United States Patent
Salkola et al.

(10) Patent No.: US 11,571,120 B2
(45) Date of Patent: Feb. 7, 2023

(54) APPARATUS AND METHOD FOR MEASURING PHYSIOLOGICAL PARAMETERS OF EYE

(71) Applicant: ICARE FINLAND OY, Vantaa (FI)

(72) Inventors: Mika Salkola, Espoo (FI); Aleksi Tamminen, Helsinki (FI)

(73) Assignee: ICARE FINLAND OY, Vantaa (FI)

( * ) Notice: Subject to any disclaimer, the term of this patent is extended or adjusted under 35 U.S.C. 154(b) by 896 days.

(21) Appl. No.: 16/462,991

(22) PCT Filed: May 8, 2018

(86) PCT No.: PCT/FI2018/050342
§ 371 (c)(1),
(2) Date: May 22, 2019

(87) PCT Pub. No.: WO2018/211169
PCT Pub. Date: Nov. 22, 2018

(65) Prior Publication Data
US 2019/0290120 A1 Sep. 26, 2019

(30) Foreign Application Priority Data

May 18, 2017 (FI) .................................... 20175448

(51) Int. Cl.
*A61B 3/00* (2006.01)
*A61B 3/10* (2006.01)
*A61B 5/0507* (2021.01)

(52) U.S. Cl.
CPC ............ *A61B 3/0025* (2013.01); *A61B 3/101* (2013.01); *A61B 3/1005* (2013.01); *A61B 5/0507* (2013.01)

(58) Field of Classification Search
CPC ... A61B 3/0025; A61B 5/0507; A61B 3/1005; A61B 3/101; A61B 18/1492;
(Continued)

(56) References Cited

U.S. PATENT DOCUMENTS

2006/0106375 A1* 5/2006 Werneth ............. A61B 18/1492
606/41
2007/0030115 A1 2/2007 Itsuji et al.
(Continued)

FOREIGN PATENT DOCUMENTS

JP 2011179902 A 9/2011
JP 2016053528 A 4/2016
WO 2017181201 A1 10/2017

OTHER PUBLICATIONS

Japan Patent Office, Notification of Ground of Rejection, Application No. 2019528894, dated Mar. 7, 2022, 4 pages.
(Continued)

*Primary Examiner* — Brandi N Thomas
(74) *Attorney, Agent, or Firm* — Ziegler IP Law Group, LLC

(57) ABSTRACT

An apparatus and a method for measuring physiological parameters of an eye. The apparatus includes a transmitter for transmitting a first set of electromagnetic waves of a first set of frequencies towards the eye, a receiver for receiving reflected electromagnetic waves corresponding to the transmitted first set of electromagnetic waves of the first set of frequencies, a comparator configured to compare the transmitted first set of electromagnetic waves with the received reflected electromagnetic waves for determining an amplitude response and a phase response for each of the electromagnetic waves of the first set of frequencies, and a calculation unit configured to fit the determined amplitude response and phase response to a physiological model of the eye to determine the physiological parameters of the eye.

9 Claims, 11 Drawing Sheets

(58) Field of Classification Search
CPC .......... A61B 2017/00106; A61B 2017/00243; A61B 2018/00351; A61B 2018/00702; A61B 2018/00791; A61B 5/14551; A61B 8/0833; A61B 2562/0233; A61B 2562/0242; A61B 2562/043; A61B 5/0002; A61B 5/14542; A61B 5/14546; A61B 5/14552; A61B 5/1464; A61B 5/252; A61B 5/4362; A61B 5/6826; A61B 5/6838; A61B 5/7232; A61B 5/7246; A61B 2560/0219; A61B 2560/0252; A61B 2560/0418; A61B 2562/0238; A61B 3/1241; A61B 3/16; A61B 5/01; A61B 5/031; A61B 5/14532; A61B 5/14539; A61B 5/1455; A61B 5/14555; A61B 5/1486; A61B 5/18; A61B 5/416; A61B 5/445; A61B 5/4839; A61B 5/6814; A61B 8/06; A61B 8/56; A61B 2560/0214; A61B 2562/12; A61B 3/0058; A61B 3/10; A61B 3/14; A61B 3/185; A61B 5/14507; A61B 5/412; A61B 2560/04; A61B 2560/0412; A61B 2560/0431; A61B 2562/0217; A61B 2562/14; A61B 2562/166; A61B 5/021; A61B 5/024; A61B 5/05; A61B 5/053; A61B 5/061; A61B 5/1117; A61B 5/14535; A61B 5/318; A61B 5/4082; A61B 5/411; A61B 5/413; A61B 5/4869; A61B 5/681; A61B 5/6821; A61B 5/6823; A61B 5/7207; A61B 8/085; A61B 8/4254

See application file for complete search history.

(56) References Cited

U.S. PATENT DOCUMENTS

| | | |
|---|---|---|
| 2008/0273171 A1 | 11/2008 | Huth et al. |
| 2009/0201465 A1 | 8/2009 | Huth |
| 2013/0162949 A1 | 6/2013 | Culjat et al. |
| 2015/0100012 A1 | 4/2015 | Muller |
| 2015/0351628 A1 | 12/2015 | Huth et al. |
| 2016/0338585 A1 | 11/2016 | Arieli et al. |

OTHER PUBLICATIONS

Taylor et al, "THz and mm-Wave Sensing of Corneal Tissue Water Content: Electromagnetic Modeling and Analysis", IEEE Transactions on Terahertz Science and Technology, pp. 170-183, Aug. 27, 2015, 37 pages.

Taylor Zachary D et al: "THz and mm-Wave Sensing of Corneal Tissue Water Content: In Vivo Sensing and Imaging Results", IEEE Transactions on Terah Ertz Science an d Technology, IEEE, Piscataway, NJ, USA, vol. 5, No. 2, Mar. 1, 2015, 14 pages.

Bennett David et al: "Assessment of corneal hydration sensing in the terahertz band:results at 100 GHz" International Society for Optical Engineering, SPIE, PO Box 10 Bellingham WA 98227-0010 USA, voL 17, No. 9, Sep. 1, 2012 XSep. 1, 2012 }, p. 97008, XP060023866, ISSN: 1083-3668, DOI: 10.1117/1 .JB0.17.9. 097008.

International Search Report and Written Opinion of the International Searching Authority, Application No. PCT/FI2018/050342, dated Oct. 18, 2018, 15 pages.

Bennett, D.B. et al. "Terahertz sensing in corneal tissues" in Journal of Biomedical Optics May 2011, vol. 16, No. 5, 057003, <DOI:10. 1117/1.3575168>.

Liu, Wen-Quan et al. "Spectroscopic measurements and terahertz imaging of the cornea using a rapid scanning terahertz time domain spectrometer" in Chinese Physics B Chinese Physical Society and IOP Publishing Ltd, Jun. 2016, vol. 25, No. 6, <DOI:10.1088/1674-1056/25/6/060702>.

Finnish Patent and Registration Office, Search Report, Application No. 20175448, dated Aug. 25, 2017, 2 pages.

\* cited by examiner

APPARATUS AND METHOD FOR MEASURING PHYSIOLOGICAL PARAMETERS OF EYE

TECHNICAL FIELD

The present disclosure relates generally to ophthalmology; and more specifically, to apparatuses and methods for measuring physiological parameters of eyes.

BACKGROUND

Presently, a growing amount of human population is suffering from serious eye diseases, such as, but not limited to, glaucoma and dry eye syndrome without necessarily even knowing it themselves. Also, refractive surgery is common and use of eye contact lenses is very popular. In order to accurately diagnose eye-related problems and diseases, analysis of properties of eyes is required. Therefore, nowadays, specialized equipment operable to measure physiological properties of the eyes, are being developed.

However, existing equipment to measure physiological properties of the eye suffer from a number of limitations. In an example, the existing equipment are based on precision optics and fine mechanics making their structure complex and expensive to manufacture. Usability often is complicated and requires special skills. In another example, existing equipment may require physical contact with the eyes for measuring the physiological parameters of the eye. However, such physical contact often leads to irritation and high risk of infection in the eyes and requires ocular anaesthesia.

Therefore, in light of the foregoing discussion, there exists a need to overcome the aforementioned drawbacks associated with existing equipment and techniques for measuring physiological properties of eyes.

SUMMARY

The present disclosure seeks to provide an apparatus for measuring physiological parameters of an eye. The present disclosure also seeks to provide a method for measuring physiological parameters of an eye. The present disclosure seeks to provide a solution to the existing problems of measurement inaccuracies, irritation and high risk of infection in eyes during measurement of physiological parameters of eyes. An aim of the present disclosure is to provide a solution that overcomes at least partially the problems encountered in prior art and provides accurate measurements of physiological parameters of eyes.

In one aspect, an embodiment of the present disclosure provides an apparatus for measuring physiological parameters of an eye, comprising
  a transmitter for transmitting a first set of electromagnetic waves of a first set of frequencies towards the eye;
  a receiver for receiving reflected electromagnetic waves corresponding to the transmitted first set of electromagnetic waves of the first set of frequencies;
  a comparator configured to compare the transmitted first set of electromagnetic waves with the received reflected electromagnetic waves for determining an amplitude response and a phase response for each of the electromagnetic waves of the first set of frequencies; and
  a calculation unit configured to fit the determined amplitude response and phase response to a physiological model of the eye to determine the physiological parameters of the eye wherein the transmitter is operable to transmit electromagnetic waves within a frequency range from 100 GHz to 1000 GHz.

In another aspect, an embodiment of the present disclosure provides a method for measuring physiological parameters of an eye, comprising
  transmitting a first set of electromagnetic waves of a first set of frequencies towards the eye at a first point of time;
  receiving reflected electromagnetic waves corresponding to the transmitted first set of electromagnetic waves of the first set of frequencies;
  determining an amplitude response and a phase response for each of the electromagnetic waves of the first set of frequencies by comparing the transmitted first set of electromagnetic waves with the received reflected electromagnetic waves; and
  determining a first set of physiological parameters of the eye by a calculation process of fitting the determined amplitude responses and phase responses to a physiological model of the eye,
wherein the transmitter is operable to transmit electromagnetic waves within a frequency range from 100 GHz to 1000 GHz.

Embodiments of the present disclosure substantially eliminate or at least partially address the aforementioned problems in the prior art and enables accurate measurement of physiological parameters of eyes in a patient/user friendly manner.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
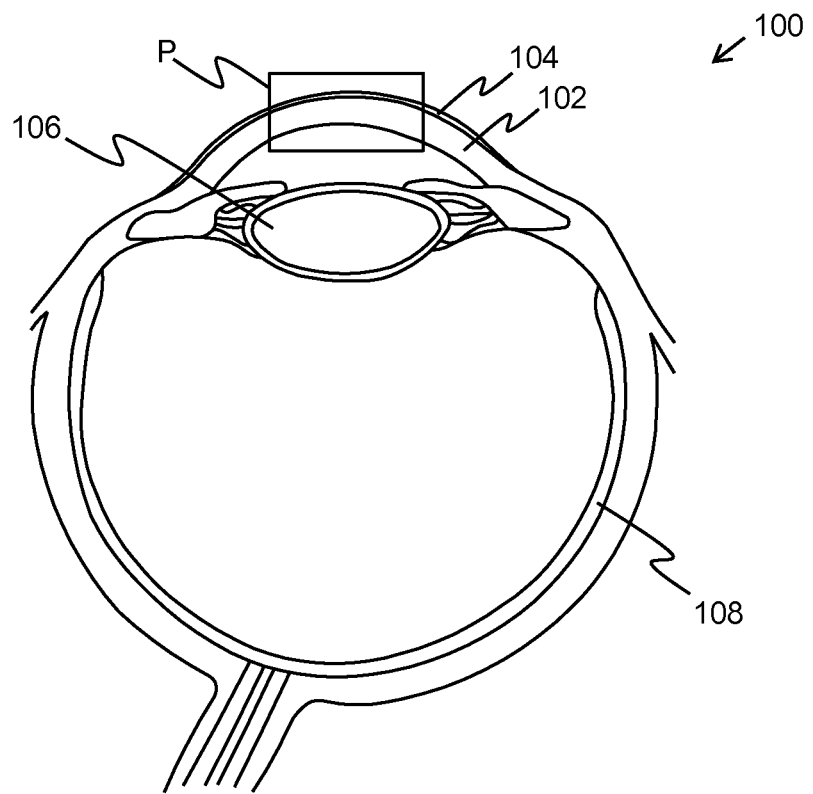
FIG. 1 illustrates a schematic illustration of anatomy of an eye, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides an apparatus for measuring physiological parameters of an eye, comprising
- a transmitter for transmitting a first set of electromagnetic waves of a first set of frequencies towards the eye;
- a receiver for receiving reflected electromagnetic waves corresponding to the transmitted first set of electromagnetic waves of the first set of frequencies;
- a comparator configured to compare the transmitted first set of electromagnetic waves with the received reflected electromagnetic waves for determining an amplitude response and a phase response for each of the electromagnetic waves of the first set of frequencies; and
- a calculation unit configured to fit the determined amplitude response and phase response to a physiological model of the eye to determine the physiological parameters of the eye, wherein the transmitter is operable to transmit electromagnetic waves within a frequency range from 100 GHz to 1000 GHz.

In another aspect, an embodiment of the present disclosure provides a method for measuring physiological parameters of an eye, comprising
- transmitting a first set of electromagnetic waves of a first set of frequencies towards the eye at a first point of time;
- receiving reflected electromagnetic waves corresponding to the transmitted first set of electromagnetic waves of the first set of frequencies;
- determining an amplitude response and a phase response for each of the electromagnetic waves of the first set of frequencies by comparing the transmitted first set of electromagnetic waves with the received reflected electromagnetic waves; and
- determining a first set of physiological parameters of the eye by a calculation process of fitting the determined amplitude responses and phase responses to a physiological model of the eye, wherein the transmitting of electromagnetic waves is carried out within a frequency range from 100 GHz to 1000 GHz.

The present disclosure provides an apparatus and a method of measuring physiological parameters of an eye. The described method includes determination of amplitude response as well as phase response for each of transmitted and reflected electromagnetic waves. Therefore, the physiological parameters of the eye, measured by employing the described method, are highly accurate and reliable. Furthermore, the described apparatus is simple to operate, inexpensive, and does not require physical contact with the eye for measuring the physiological parameters of the eye. Therefore, the described apparatus is operable in a user/patient friendly manner.

It is to be understood that the term 'physiological parameters of an eye' used herein relates to properties of various components of the eye, for example, properties of a cornea of the eye, tear film of the eye, and so forth. According to an embodiment of the present disclosure, the physiological parameters of the eye are at least one of thickness of the cornea ($d_t$), corneal tissue water content (m) and thickness of tear film ($d_s$). Optionally, the physiological parameters of the eye may further include at least one of thickness of cornea epithelium, thickness of Bowman's membrane, thickness of stroma of the cornea, thickness of Dua's layer, thickness of Descemet's membrane and thickness of corneal endothelium. Optionally, the physiological parameters of the eye may further comprise at least one of thickness of lipid layer of the tear film, thickness of water layer of the tear film and thickness of mucus layer of the tear film. According to an embodiment, the apparatus can be configured to measure physiological parameters of an eye of a human or an animal.

An apparatus for measuring physiological parameters of the eye comprises a transmitter for transmitting a first set of electromagnetic waves of a first set of frequencies towards the eye. Specifically, the apparatus is arranged so as to direct the first set of electromagnetic waves, via the transmitter, onto the eye of a person. The transmitter is configured to transmit electromagnetic waves of different (or various) frequencies. In an example, the transmitter may be a terahertz transmitter that may be operable to transmit the electromagnetic waves greater than and/or equal to 1 THz (or 1000 GHz).

The specified wavelengths of the electromagnetic waves in the present disclosure have to be harmless to patients (eye-safe) and to equipment users. The specified wavelengths in the present disclosure are eye-safe, because the wavelength range is strongly absorbed in the eye's cornea and in the aqueous anterior segment of an eye and therefore with practical transmission power cannot reach the significantly more sensitive retina. Because of the low transmission power, the absorbance of the electromagnetic waves specified in the present disclosure do not meaningfully increase the temperature of eye tissue where the absorbance takes place. Also, the specified wavelengths in the present disclosure are considered as non-ionizing radiation. To summarize, the specified wavelengths in the present disclosure with the practical transmission power do not result in eye tissue destruction or harm such as, but not limited to, direct killing of cells, changes in cellular DNA that could produce lethal or other mutations or thermal induced changes or damage.

Very meaningful to patient friendliness is that the specified wavelengths in the present disclosure are out of the visual range of any animal and human. Invisible wavelengths do not have irritating effects or draw patients' attention during the measurement event and therefore increase significantly user and patient friendliness.

From technical point of view, frequencies must be selected so that the measured amplitude and phase responses can be separated from the equipment noise level with sufficient marginal. Preferably, the sufficient marginal is possible to achieve when the electrical thickness of the layer is of the order of a quarter wavelength. Depending on the algorithm used to find the desired properties of the eye, also an electrical layer thickness less than a quarter wavelength may be possible to determine. When the electrical thickness of the layer equals or is greater than half a wavelength, the measured response may be ambiguous and this limit sets the longest wavelength corresponding to the selected frequency.

For a typical cornea dimensions, the stroma is the thickest layer, about 500 μm (micrometer), and it corresponds to lower frequency limit of 200 GHz. The thinnest layer in the corneal is of the order of 10 μm, and it corresponds to highest frequency limit of 10 THz. The corneal tissue transmission at the selected frequency may limit the available range of usable frequencies and 1000 GHz is considered as the practical upper limit for corneal tissue measurement.

Optionally, the transmitter is operable to transmit the electromagnetic waves within a frequency range from 100 GHz to 1000 GHz. In such instance the electromagnetic waves have wavelengths ranging from 0.3 millimeter (corresponding to 1000-GHz frequency) to 3 millimeter (corresponding to 100-GHz frequency). It is to be understood that wavelengths of the electromagnetic waves in a medium may be calculated as a function of frequency by employing the following equation:

$$\lambda = c/(f \times \sqrt{n})$$

wherein 'c' denotes speed of light in vacuum and is approximately equivalent to $3*(10^8)$ metres per second, 'f' is the frequency of the electromagnetic wave, n is the refractive index of the medium, and 'λ' is the wavelength of the electromagnetic wave.

More optionally, the transmitter is operable to transmit electromagnetic waves within a frequency range from 200 GHz to 400 GHz. For example, the transmitter may transmit electromagnetic waves within a frequency range from 200 GHz to 250 GHz. In operation, the transmitter transmits the first set of electromagnetic waves towards the eye. It is to be understood that the transmitter may be operable to transmit various sets of frequencies for facilitating measurement of physiological parameters of the eye. Therefore, the first set of electromagnetic waves includes the electromagnetic waves of the first set of frequencies, wherein the first set of frequencies includes frequencies within the aforementioned frequency ranges.

According to an embodiment, the transmitter may be operable to transmit the electromagnetic waves within a frequency range from 100, 150, 200, 250, 300, 400, 450, 500, 600, 650, 700, 800, 850 or 900, GHz up to 150, 200, 250, 300, 400, 450, 500, 600, 650, 700, 800, 850, 900 or 1000 GHz.

According to an embodiment, the first set of frequencies may be a sweep and the sweep may be one of a continuous sweep, a discrete sweep, a broadband sweep or a frequency hopping. Specifically, the transmitter may transmit the first set of electromagnetic waves as the sweep. It is to be understood that the term 'sweep' refers to a signal, wherein frequency of the signal varies between a first frequency value (or a start frequency) and a second frequency value (or an end frequency) or in a frequency hopping a set of predefined frequencies in any order.

In an example, the first set of frequencies may be the continuous sweep. In such example, the continuous sweep may extend from electromagnetic waves of a start frequency (such as 200 GHz) to electromagnetic waves of an end frequency (such as 325 GHz). In such continuous sweep, variation in frequencies is implemented an analogous manner, by employing an analogue sweep signal. Beneficially, the continuous sweep is fast and includes even minute frequency variations, thereby providing high-resolution electromagnetic signals in a single sweep.

In another example, the first set of frequencies may be the discreet sweep. In such example, the discrete sweep may extend from electromagnetic waves of a start frequency (such as 200 GHz) to electromagnetic waves of an end frequency (such as 250 GHz). In such discrete sweep, the variation in the frequencies is carried out in discrete steps, wherein variation between any two discrete frequencies may be implemented after equal or unequal time intervals. Optionally, the discrete frequency steps may be equal or unequal. For example, in the exemplary discrete sweep, variation in frequencies may be carried out in equal discrete frequency steps such as 200 GHz, 205 GHz, 210 GHz, 215 GHz, 220 GHz, 225 GHz, 230 GHz, 235 GHz, 240 GHz, 245 GHz, and 250 GHz. It is to be understood that although 5 GHz frequency steps are described in the given example, different step intervals may be employed as per requirement.

In yet another example, the first set of frequencies may be the broadband sweep. In such example, the broadband sweep may extend from electromagnetic waves of a start frequency (such as 200 GHz) to electromagnetic waves of an end frequency (such as 250 GHz). Furthermore, the first set of electromagnetic waves employing the broadband sweep, are transmitted by the transmitter at the same time. Optionally, the transmitter may employ mathematical convolution method to avoid frequency mixing between the first set of electromagnetic waves that are transmitted as the broadband sweep. For example, various frequencies such as 205 GHz, 210 GHz, 215 GHz, 220 GHz, 225 GHz, 230 GHz, 235 GHz, 240 GHz, 245 GHz, and 250 GHz are transmitted simultaneously using the broadband sweep. In such instance, the transmitter may be a broadband transmitter.

Optionally, the sweep comprises at least one frequency per two unknown parameters in the physiological model of the eye. Specifically, a single frequency of the sweep may facilitate in providing an amplitude response and a phase response corresponding thereto. Therefore, every frequency constituting the sweep may provide two-faceted information pertaining thereto, namely, the amplitude response, and the phase response. Consequently, every frequency of the sweep may be employed for determining two unknown parameters in the physiological model of the eye.

The apparatus for measuring physiological parameters of the eye further comprises a receiver for receiving the reflected electromagnetic waves corresponding to the transmitted first set of electromagnetic waves of the first set of frequencies. Specifically, the apparatus is arranged so as to receive the reflected electromagnetic waves from the eye onto the receiver. More specifically, the first set of electromagnetic waves of the first set of frequencies is reflected from a surface of the eye and the reflected electromagnetic waves corresponding to the transmitted first set of electromagnetic waves of the first set of frequencies are received by the receiver. In an embodiment, the transmitter and the receiver may be a single unit, such as a transceiver.

The apparatus for measuring physiological parameters of the eye further comprises a comparator configured to compare the transmitted first set of electromagnetic waves with the received reflected electromagnetic waves for determining an amplitude response and a phase response for each of the electromagnetic waves of the first set of frequencies. Specifically, the comparator compares parameters such as amplitude values and phase values of the transmitted first set of electromagnetic waves and the received reflected electromagnetic waves. Furthermore, the comparator may receive such parameters from the transmitter and the receiver. Therefore, in an embodiment, the receiver and the transmitter may be communicably coupled with the comparator. In another embodiment, the receiver and the transmitter may be hardwired with the comparator.

According to an embodiment, the comparator is configured to determine the amplitude response for each of the first set of electromagnetic waves of the first set of frequencies by comparing amplitudes of the transmitted first set of electromagnetic waves with amplitudes of the received reflected electromagnetic waves; as well as the phase response for each of the first set of electromagnetic waves of the first set of frequencies by comparing phases of the transmitted first set of electromagnetic waves with phases of the received reflected electromagnetic waves. Specifically, the comparator may determine the amplitude response and the phase response by calculating difference between amplitude values and phase values of the transmitted first set of electromagnetic waves with amplitude values and phase values of the received reflected electromagnetic waves. In an embodiment, the aforesaid difference between the amplitude and the phase values may be computed as an absolute value.

It is to be understood that the term 'amplitude response' used herein relates to a relationship between the compared amplitudes of the transmitted first set of electromagnetic waves of the first set of frequencies and the corresponding received reflected electromagnetic waves, as a function of frequency. Similarly, it is to be understood that the term 'phase response' used herein relates to a relationship between phase differences of the transmitted first set of electromagnetic waves of the first set of frequencies and the corresponding received reflected electromagnetic waves, as the function of frequency. In an embodiment, alternatively, or additionally, the term 'amplitude response' may relate to amplitude of the received reflected electromagnetic waves (corresponding to the transmitted first set of electromagnetic waves of the first set of frequencies), as a function of frequency.

The apparatus for measuring physiological parameters of the eye further comprises a calculation unit configured to fit the determined amplitude response and phase response to a physiological model of the eye to determine the physiological parameters of the eye. Specifically, the calculation unit may be hardware, software, firmware, or a combination of these, operable to fit the determined amplitude response and phase response to the physiological model of the eye.

In an embodiment, the physiological model of the eye comprises physiological model parameters, wherein the physiological model parameters relate to attributes of the various components of the eye, as described above.

In an embodiment, the physiological model of the eye is pre-programmed in the calculation unit. In such embodiment, values of the physiological model parameters may be fixed and/or variable. For example, the values of the physiological model parameters may be automatically/manually updated several times. In an embodiment, the apparatus may be communicably coupled to a remote server via a network, such as the internet. In such embodiment, the values of the physiological model parameters may be updated at the calculation unit from the remote server. Additionally, or alternatively, in such embodiment, the remote server may be configured to fit the determined amplitude response and phase response to a physiological model of the eye. In another embodiment, the values of physiological model parameters may be updated by a user of the calculation unit and/or the remote server.

In an embodiment, the physiological model of the eye is further configured to have a layer in front of the eye, wherein the layer corresponds to contact lens properties. Specifically, in such embodiment the physiological model of the eye is adapted to accommodate for physical properties of the contact lens during determination of the physiological parameters of the eye. More specifically, the layer in front of the eye is configured to have physical properties similar to the contact lens properties. Beneficially, such embodiment may be employed to determine physiological parameters of an eye of a person wearing contact lenses. Therefore, such physiological model including the layer in front of the eye provides accurate values of the physiological parameters of the eye.

According to an embodiment, the apparatus may further comprise a user interface to provide an output of the measured physiological parameters of the eye. Optionally, the user interface may be communicably coupled to the calculation unit. In another embodiment, the user interface may be rendered on a portable device communicably coupled to the apparatus. Specifically, the portable device may be wirelessly coupled to the apparatus.

A method for measuring physiological parameters of the eye comprises transmitting the first set of electromagnetic waves of the first set of frequencies towards the eye at a first point of time. Specifically, such transmission is performed by the aforementioned transmitter. The method further comprises receiving the reflected electromagnetic waves corresponding to the transmitted first set of electromagnetic waves of the first set of frequencies. Specifically, the receiver described previously herein, is employed for such receiving. Thereafter, the method comprises determining the amplitude response and the phase response for each of the electromagnetic waves of the first set of frequencies by comparing the transmitted first set of electromagnetic waves with the received reflected electromagnetic waves. Specifically, such comparison is performed by the aforesaid comparator. Furthermore, the method comprises determining a first set of physiological parameters of the eye by a calculation process of fitting the determined amplitude responses and phase responses to the physiological model of the eye. Specifically, the aforementioned calculation unit is configured to implement the aforesaid calculation process to determine the first set of physiological parameters of the eye.

In an embodiment, the determination of the amplitude response and phase response comprises steps of comparing amplitudes of the transmitted first set of electromagnetic waves with amplitudes of the received reflected electromagnetic waves to determine the amplitude response for each of the first set of electromagnetic waves of the first set of frequencies; as well as comparing phases of the transmitted first set of electromagnetic waves with phases of the received reflected electromagnetic waves to determine the phase response for each of the first set of electromagnetic waves of the first set of frequencies. Specifically, such determination of the amplitude response and phase response is performed by the comparator.

In an embodiment, the determining of physiological parameters of the eye is done by the calculation process of calculating a first set of model based amplitude response and phase response using the physiological model of the eye, using a first set of parameters; comparing the first set of model based amplitude response and phase response with the determined amplitude response and phase response to calculate to calculate a first deviation value there between, wherein if the first deviation value is within a predetermined range, the first set of parameters is the first set of physiological parameters of the eye, and if the first deviation value is outside the predetermined range, the method further comprises selecting a second set of parameters; calculating a second set of model based amplitude responses and phase responses using the physiological model of the eye, using the second set of parameters; comparing the second set of model based amplitude responses and phase responses with the determined amplitude responses and phase responses to calculate a second deviation value therebetween.

In an embodiment, the first set of parameters relates to attributes of the various components of the eye. Specifically, the physiological model of the eye may comprise values and/or ranges of the first set of parameters. In an example, a range of the first set of parameters such as, but not limited to, the thickness of the cornea (dt), the corneal tissue water content (m), and the thickness of tear film ($d_s$) may be randomly selected. In another example, values/ranges of the first set of parameters may be selected as typical values/ranges expected to be associated with the eye. For example, for an eye of a 45 year old person, a value of the thickness of the cornea ($d_t$) may be 545 micro meters.

In an embodiment, the first set of model based amplitude response and phase response may be calculated using a reflectometer model, and the physiological model of the eye. It is to be understood that the term 'reflectometer model' relates to a computational model of a reflectometer such that the reflectometer model represents a simulation of optical path of the transmitted and received electromagnetic waves towards and from the physiological model of eye, respectively. It is to be understood that in the simulation of the optical path of the transmitted set of electromagnetic waves towards the physiological model of the eye, the set of electromagnetic waves are transmitted at a same frequency as transmitted by the transmitter towards the eye. For example, if the transmitter transmits the first set of electromagnetic waves of a first set of frequencies (between 200 GHz-240 GHz) towards the eye, then the reflectometer model also simulates the optical path of electromagnetic waves towards the physiological model of eye with the first set of frequencies (i.e. between 200 GHz-240 GHz).

In an embodiment, calculation of the first deviation value between the first set of model based amplitude and phase response, and the determined amplitude response and phase response, may be implemented by the calculation unit. Specifically, the calculation unit may compare amplitude value and phase value of the simulated electromagnetic wave that is transmitted towards the physiological model of eye with amplitude value and phase value of the received reflected electromagnetic wave from the physiological model of eye. The calculation unit then determines the first set of model based amplitude response and phase responses of the physiological model of the eye by calculating a difference between aforesaid amplitude and phase values of the simulated transmitted electromagnetic waves with the simulated reflected electromagnetic waves. Thereafter, the calculation unit compares the determined first set of model based amplitude response and the model based phase response with the determined amplitude response and the determined phase response calculated by the comparator, for the corresponding set of frequencies to calculate the first deviation value there between. If the first deviation value is within a predetermined range, then the first set of parameters of the physiological model are the physiological parameters of the eye. In an embodiment, the predetermined range may be pre-programmed into the calculation unit.

In the aforesaid embodiment, if the first deviation value is outside the predetermined range, the second set of parameters may be selected by the calculation unit. Further, the second set of model based amplitude responses and model based phase responses may be determined and compared with the determined amplitude responses and determined phase responses respectively to calculate the second deviation value therein. If the second deviation value is within the predetermined range, then the second set of parameters of the parameters of the physiological model are the physiological parameters of the eye. On the contrary, if the second deviation value is also outside the predetermined range, the above process may be followed iteratively. Therefore, if the second deviation value is outside the predetermined range, various techniques such as, but not limited to, particle swarm optimization and Monte-Carlo optimisations may be used to iteratively fit the determined amplitude response and phase response to the physiological model of the eye.

According to an embodiment, a second set of frequencies may be used for measuring the first set of physiological parameters of the eye, if the deviation value is not within the predetermined range after a predetermined number of iteration rounds. Specifically, if the deviation value is still not within the predetermined range after the predetermined number of iteration rounds, a second set of frequencies may be used to determine the physiological parameters of the eye. In such instance, the second set of frequencies is used to determine the first set of physiological parameters of the eye. Optionally, the calculation unit may be configured to send the determined amplitude response and phase response along with the model based amplitude response and phase response to the remote server for determining the physiological parameters of the eye.

Optionally, the method further comprises measuring a second set of physiological parameters of the eye at a second point of time; and determining from the first set of physiological parameters and the second set of physiological parameters an evaporation rate of a tear film. More optionally, the measurement of the first set of physiological parameters and of the second set of physiological parameters is carried out during a time the eye is open and between two blinks of the eye. Specifically, during the time the eye is open, the thickness of the tear film on the cornea of the eye may reduce. For example, the first set of physiological parameters may be determined at a first point of time T1 and the second set of the physiological parameters may be determined at a second point of time T2, wherein the second point of time T2 is 2 seconds after the first point of time T1. Therefore, within the 2 second interval between the second point of time T2 and the first point of time T1, moisture content of the tear film may reduce. A difference between a value of moisture content of the tear film between time T1 and T2 may be determined using the first and second sets of physiological parameters. Thus, evaporation rate may also be deduced, as a function of time difference between the second point of time T2 and the first point of time T1.

Experimental Part

To further describe benefits of measuring both the amplitude and the phase response, a set of signal to noise ratio (SNR) simulations and measurements were performed. Basically, the present Experimental part is related to difference between performing measurements using incoherent technology and coherent technology. The incoherent technology is also called as direct detection wherein the receiver does not have phase reference from the transmitter. The coherent technology refers to setup wherein phase reference from the transmitter is available as well as phase detection with the receiver in addition to amplitude information.

Depending on a setup, the received signal has certain signal-to-noise ratio (SNR). The noise affects the accuracy of the measured amplitude and phase. Table 1 shows the amplitude and phase noise components for different signal-to-noise ratio values. For example, in situation where the SNR is 30 dB, relative amplitude differences below 1.3% and phase differences below 0.7 degree are not separated from noise. Typically, incoherent receivers suffer from poorer SNR than coherent ones since their noise bandwidth is not so well controlled.

TABLE 1

RMS values of relative amplitude and phase noise for different SNR.

| SNR (dB) | $a_n$ (%) | $p_n$ (°) |
|---|---|---|
| 0 | 38.59 | 26.13 |
| 5 | 22.56 | 13.49 |
| 10 | 12.83 | 7.45 |
| 15 | 7.22 | 4.18 |
| 20 | 4.09 | 2.33 |
| 25 | 2.30 | 1.32 |
| 30 | 1.29 | 0.74 |
| 35 | 0.73 | 0.42 |
| 40 | 0.41 | 0.23 |
| 45 | 0.23 | 0.13 |
| 50 | 0.13 | 0.07 |
| 55 | 0.07 | 0.04 |
| 60 | 0.04 | 0.02 |

In the present Example 1, a set of measurement data associated with a measurement set of 200-225 GHz (first set, FIGS. 8A and 8B), 200-250 GHz (second set, FIGS. 9A and 9B), 200-300 GHz (third set, FIGS. 10A and 10B) and 200-400 GHz (fourth set, FIGS. 11A and 11B) was analysed. Physiological parameters of central corneal thickness (CCT), corneal-tissue water content (CTWC) and tear-film thickness were fitted to the measurement data associated with each set. FIGS. 8A, 9A, 10A and 11A are illustrations of amplitude mean deviations when CCT and CTWC change from a central value. FIGS. 8B, 9B, 10B and 11B are illustrations of phase mean deviations when CCT and CTWC change from a central value. Two sets of cornea parameters are marked with "+": [CCT=500 μm, CTWC=50%] and [CCT=440 μm, CTWC=54%]. Clearly, when the deviation is small, the device is not capable of recording the change of parameters (i.e. change in transmitted signal in relation to received signal). It can be considered that when the deviation is smaller than the noise level either in amplitude or phase, the device might not operate accurately or at all. Further, based on the sets it can be seen that measuring bandwidth of at least 100 GHz (200-300 GHz as per FIG. 10B) is more accurate than measuring bandwidth of 50 GHz or 25 GHz.

Figure 12A:
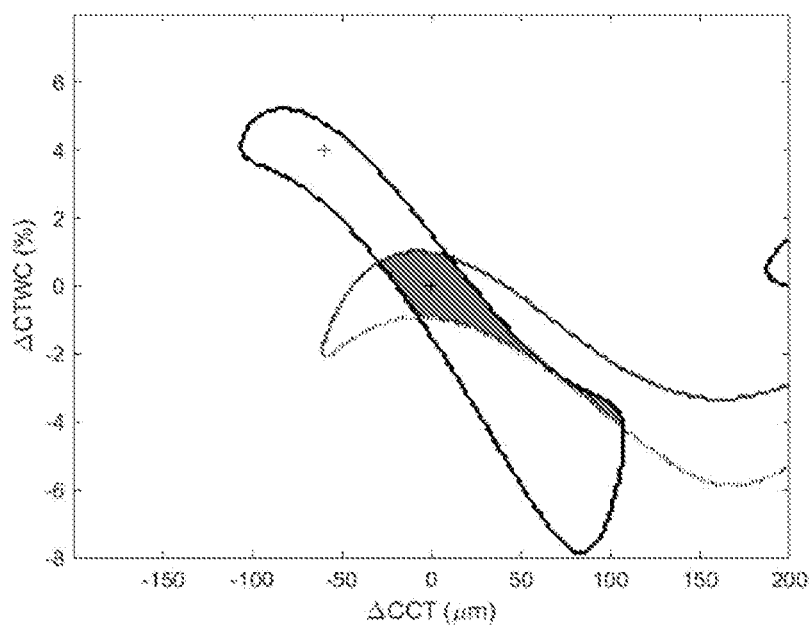
FIGS. 12A and 12B are first and second illustrations for an invalid region for amplitude, phase, and combined (gray) measurements at about 35 dB SNR.
Figure 12B:
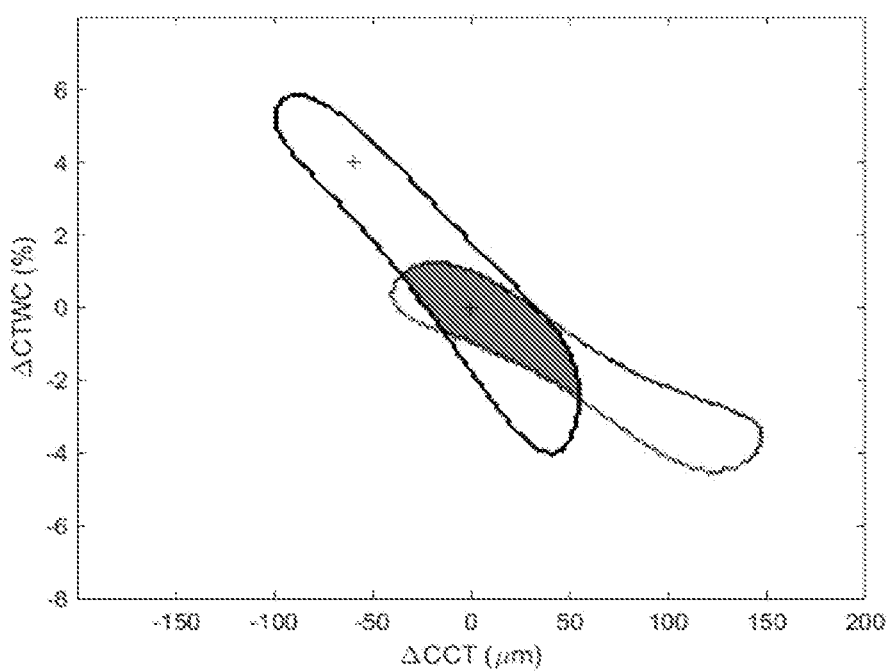
Figure 12C:
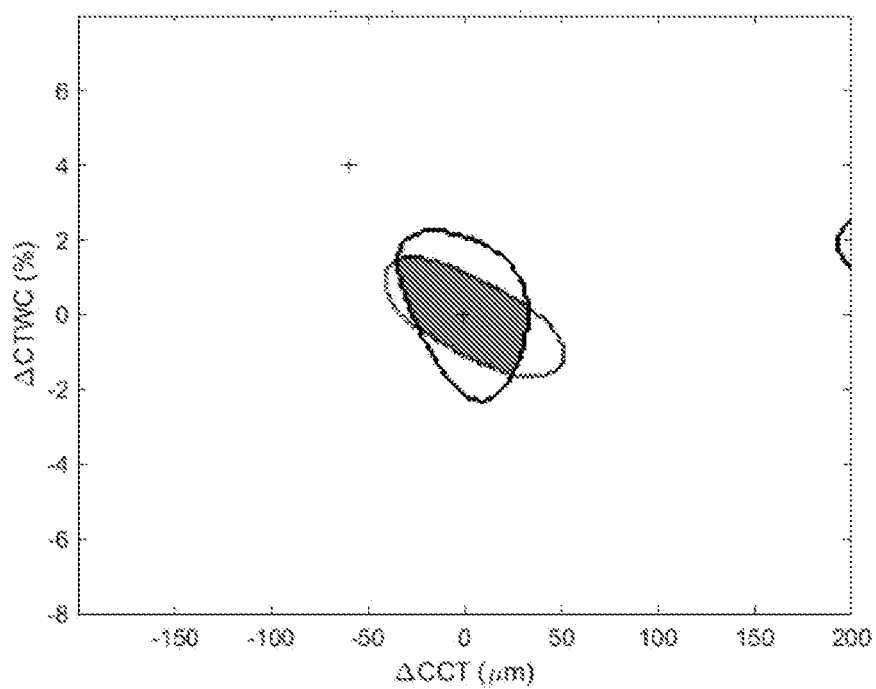
FIG. 12C and 12D are third and fourth illustrations (with grey shading) for an invalid region for amplitude, phase, and combined (gray) measurements at about 35 dB SNR.
Figure 12D:
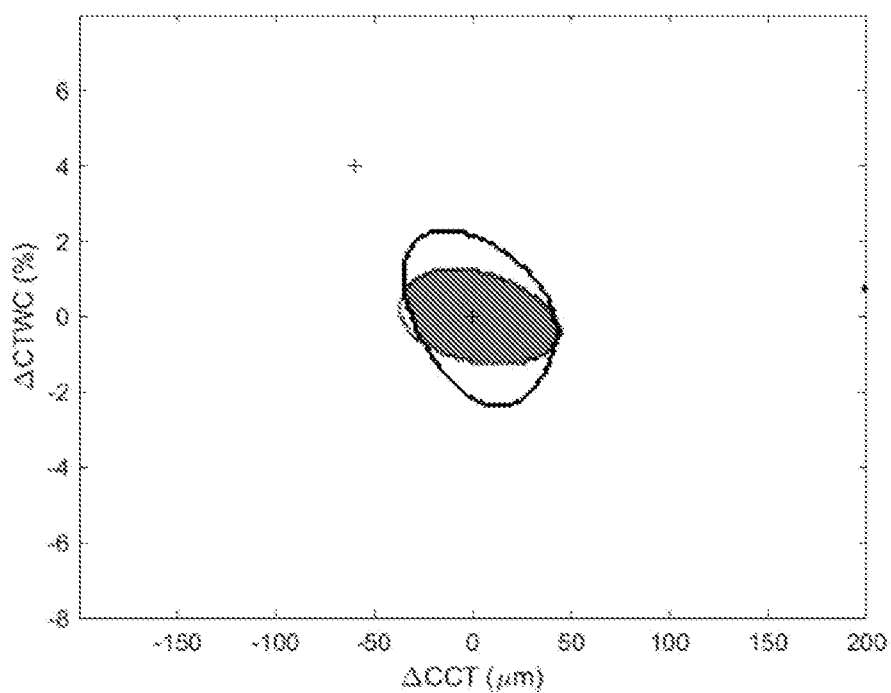

Depending on the SNR, the contours can be divided to valid and invalid regions. A valid region is where the amplitude or phase deviation is above the noise level. In an invalid region, the measurement fails (indicated with reference 800 in FIGS. 8A and 8B, reference 900 in FIGS. 9A and 9B, reference 1000 in FIGS. 10A and 10B, reference 1100 in FIGS. 11A and 11B. In said regions/areas SNR is about 35 dB). An amplitude or phase measurement alone results in invalid regions that typically cover different parameter spaces. Combination of both measurements reduces the invalid region considerably, allowing relaxed requirements for the device SNR and bandwidth, as illustrated in FIG. 12A (for the first set), FIG. 12B (for the second set), FIG. 12C (for the third set) and FIG. 12D (for the fourth set) with grey shading. The combined measurement is particularly beneficial with a relatively narrow-band measurements, where the invalid region overlap is small compared to the individual measurements.

Figure 13A:
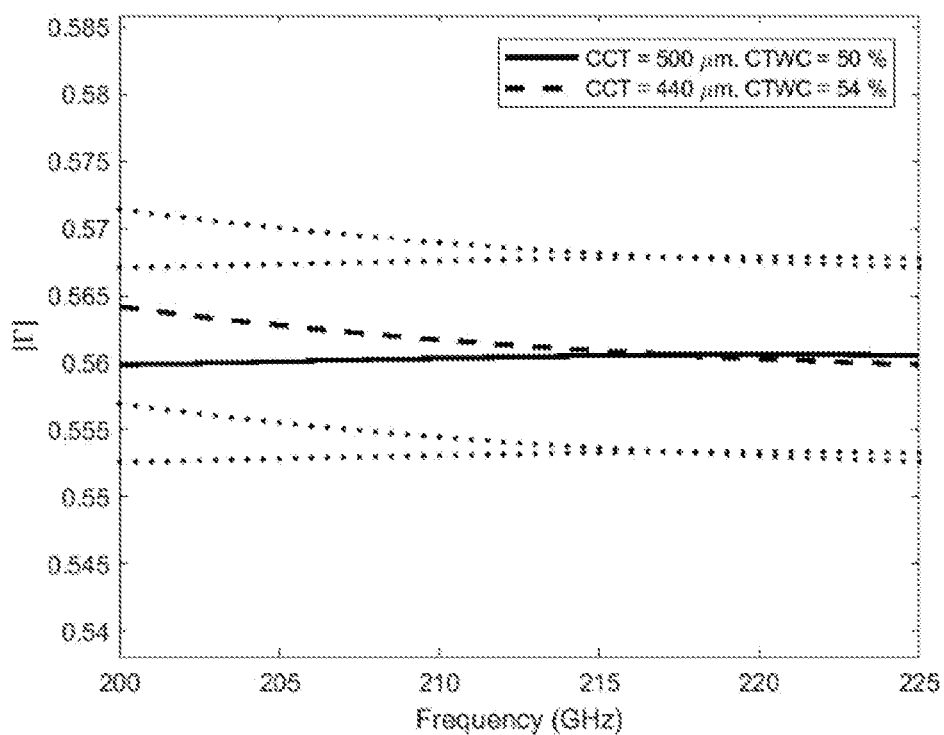
FIGS. 13A and 13B are illustrations of amplitude and phase responses across bandwidth of 25 GHz.
Figure 13B:
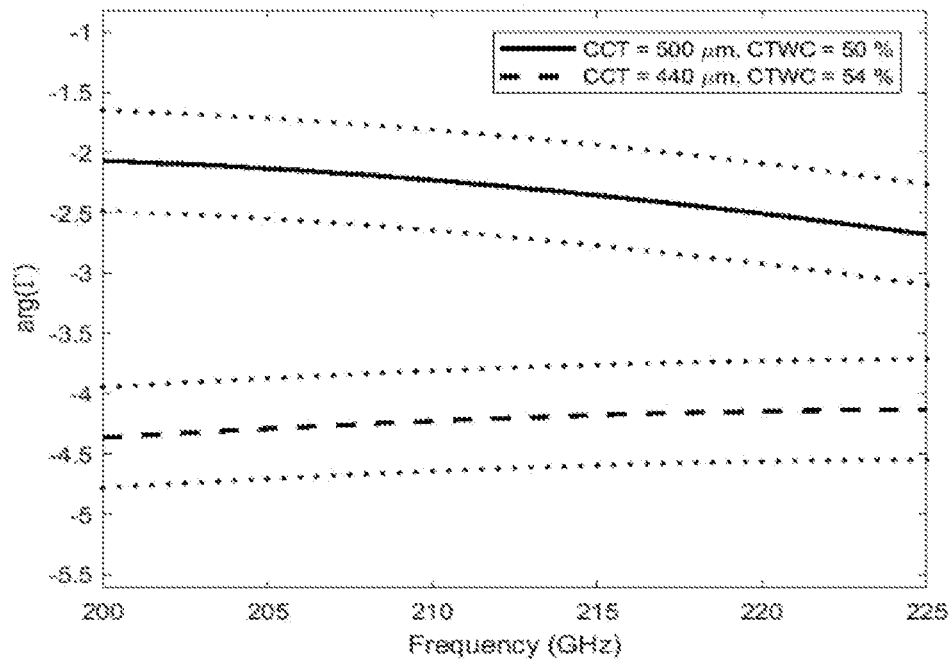

FIG. 13A is an illustration the amplitude response and FIG. 13B is an illustration of frequency response, for the corneas with the physiological parameters as described above and marked with "+" in FIGS. 8A, 8B, 9A, 9B, 10A, 10B, 11A and 11B. The responses are for two sets of cornea parameters (solid and dashed), which lie in the invalid region in amplitude. The uncertainty in amplitude and phase (RMS value of noise) are shown with dotted line above and below the responses. Clearly, the difference in amplitude responses is close to or below the noise whereas in phase they are separated. The amplitude responses are difficult to separate from each other since they are within the RMS value of the amplitude noise. However, in the phase response, there is clear margin between the responses from the two different corneas. Thus, using both amplitude and phase allows more robust measurements.

DETAILED DESCRIPTION OF THE DRAWINGS

Referring to FIG. 1, illustrated is a schematic illustration of anatomy of an eye 100 (of a human), in accordance with an embodiment of the present disclosure. As shown, the eye 100 includes a cornea 102 through which light from an environment is received by the eye 100. Further, the eye 100 is shown to include a tear film 104 on a surface of the cornea 102 that is exposed to the environment. Further, the eye 100 includes components such as a lens 106, and a retina 108.

Figure 2:
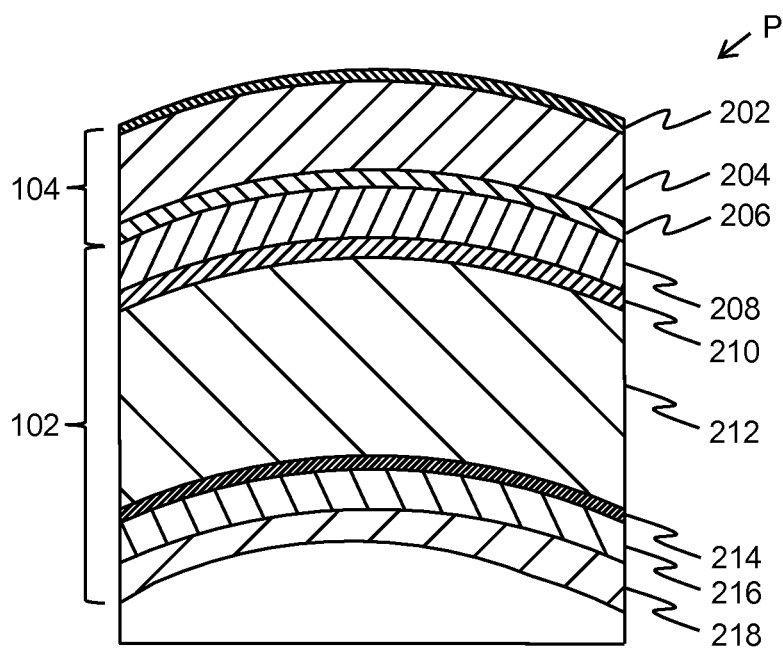
FIG. 2 is an enlarged view of a portion of the eye of FIG. 1 depicting various components of the eye, in accordance with an embodiment of the present disclosure.

Referring to FIG. 2, illustrated is an enlarged view of a rectangular portion P of the eye 100 of FIG. 1 depicting various components of the eye 100, in accordance with an embodiment of the present disclosure. Specifically, the cornea 102 and the tear film 104 of the eye 100 include various layers as depicted herein. The layers of the tear film 104 of the eye 100 include a lipid layer 202, a water layer 204, and a mucus layer 206. Further, the layers of the cornea 102 of the eye 100 include cornea epithelium 208, Bowman's membrane 210, stroma 212, Dua's layer 214, Descemet's membrane 216, and corneal endothelium 218.

Figure 3:
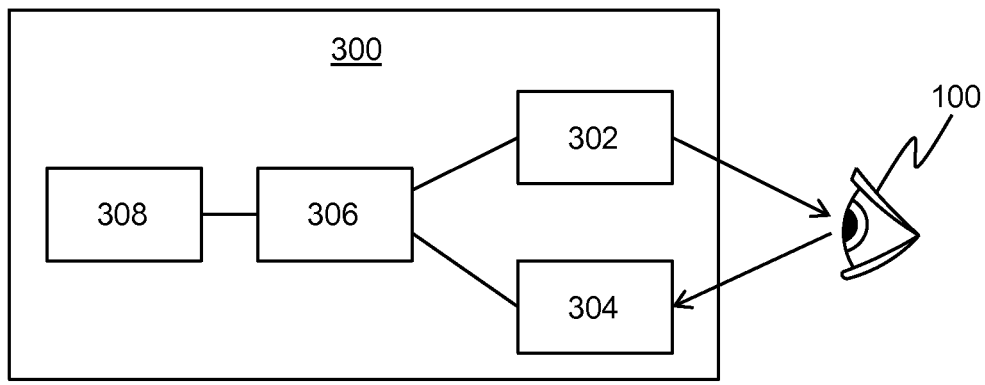
FIG. 3 is an exemplary implementation of an apparatus for measuring physiological parameters of the eye, in accordance with an embodiment of the present disclosure.

Referring to FIG. 3, illustrated is an exemplary implementation of an apparatus 300 for measuring physiological parameters of the eye 100, in accordance with an embodiment of the present disclosure. As shown, the apparatus 300 includes a transmitter 302 for transmitting a first set of electromagnetic waves of a first set of frequencies towards the eye 100, a receiver 304 for receiving reflected electromagnetic waves corresponding to the transmitted first set of electromagnetic waves of the first set of frequencies, a comparator 306 configured to compare the transmitted first set of electromagnetic waves with the received reflected electromagnetic waves for determining an amplitude response and a phase response for each of the electromagnetic waves of the first set of frequencies, and a calculation unit 308 configured to fit the determined amplitude response and phase response to a physiological model to determine the physiological parameters of the eye 100. As shown, the comparator 306 is operatively coupled to the transmitter 302, the receiver 304, and the calculation unit 308.

Figure 4:
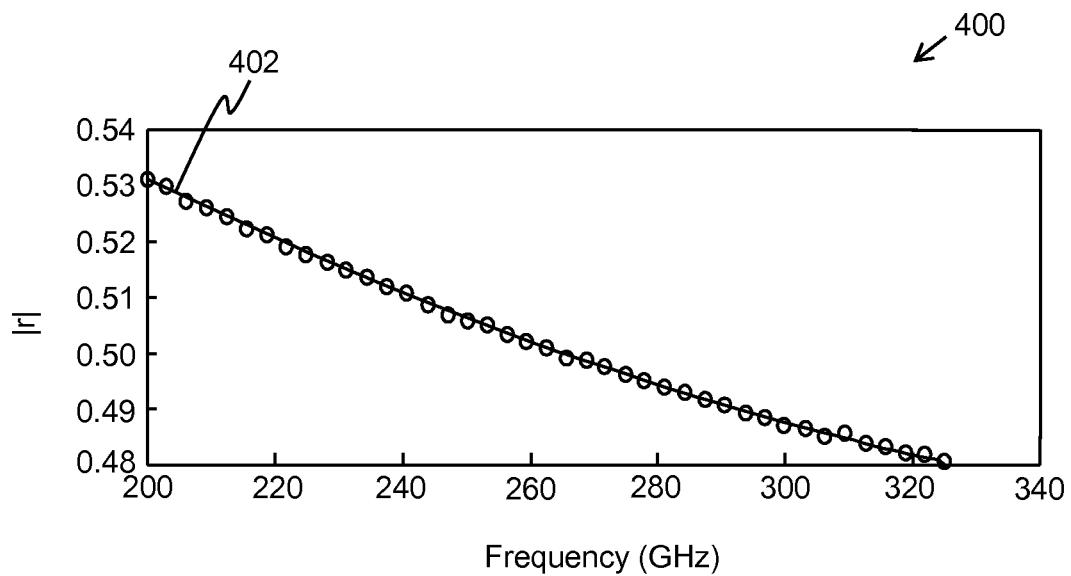
FIG. 4 is a graphical representation of an amplitude response, in accordance with an embodiment of the present disclosure.

Referring to FIG. 4, illustrated is a graphical representation of an amplitude response 400, in accordance with an embodiment of the present disclosure. Specifically, the amplitude response 400 represents a relationship between compared amplitudes of transmitted and received reflected electromagnetic waves, as a function of frequency. For example, in FIG. 4, a vertical axis of the amplitude response 400 represents amplitude of the received reflected electromagnetic waves and/or a difference between amplitudes of the transmitted and received reflected electromagnetic waves. Further, a horizontal axis of the amplitude response 400 represents a set of frequencies of the transmitted and received reflected electromagnetic waves. Optionally, as shown, such set of frequencies is a discrete sweep such as a sweep between 200 gigahertz and 325 gigahertz. Furthermore, in the amplitude response 400, measured amplitude magnitudes and/or difference between amplitudes are depicted as circles and a line 402 proximal to the circles represents fitting of the amplitude response 400 to a physiological model (not shown) to determine the physiological parameters of the eye 100.

Figure 5:
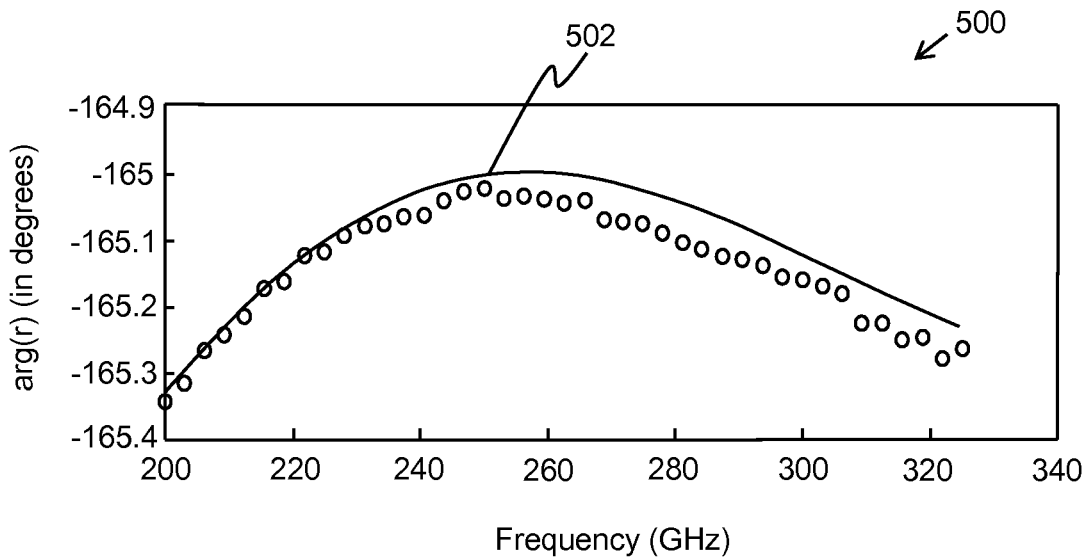
FIG. 5 is a graphical representation of a phase response, in accordance with an embodiment of the present disclosure.

Referring to FIG. 5, illustrated is a graphical representation of a phase response 500, in accordance with an embodiment of the present disclosure. Specifically, the phase response 500 represents a relationship between phase differences of transmitted and received reflected electromagnetic waves, as a function of frequency. For example, in FIG. 5, a vertical axis of the phase response 500 represents a magnitude of phase difference between the transmitted and received reflected electromagnetic waves. Further, a horizontal axis of the phase response 500 represents a set of frequencies of the transmitted and received reflected electromagnetic waves. Optionally, as shown, such set of frequencies is a discrete sweep such as a sweep between 200 gigahertz and 325 gigahertz. Furthermore, in the phase response 500, measured phase differences are depicted as circles and a line 502 proximal to the circles represents fitting of the phase response 500 to a physiological model (not shown) to determine the physiological parameters of the eye 100.

Figure 6:
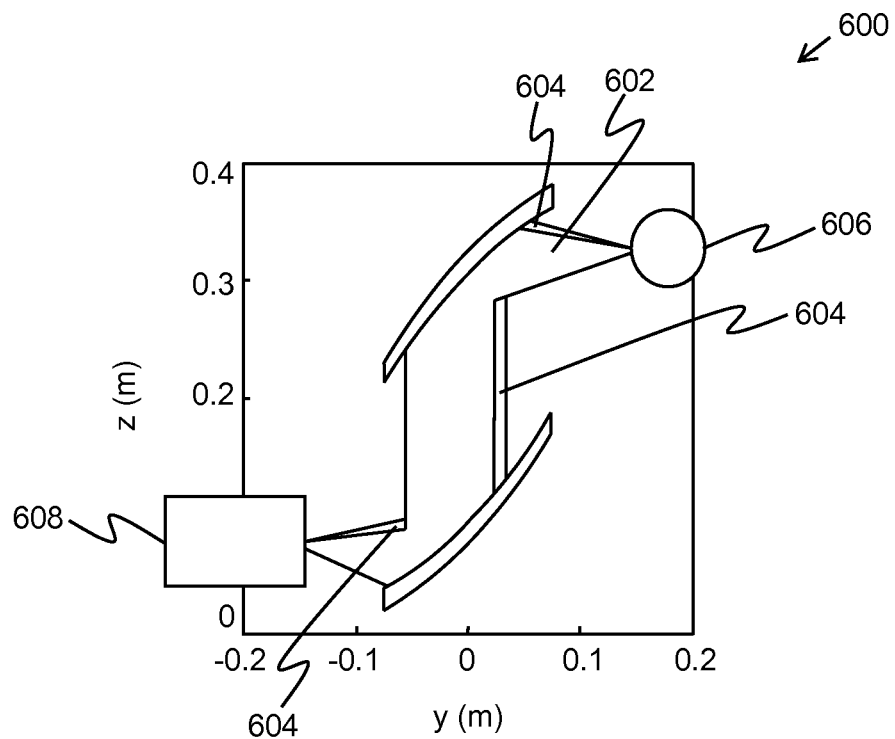
FIG. 6 is a schematic illustration of an exemplary reflectometer model, in accordance with an embodiment of the present disclosure.

Referring to FIG. 6, illustrated is a schematic illustration of an exemplary reflectometer model 600, in accordance with an embodiment of the present disclosure. Specifically, the reflectometer model 600 represents a simulation of signal paths of a transmitted first set of electromagnetic waves 602 towards a physiological model 606 of the eye 100 (shown in FIG. 1), and signal paths of received reflected electromagnetic waves 604 corresponding to the transmitted first set of electromagnetic waves. More specifically, the apparatus 300 (shown in FIG. 3) for measuring physiological parameters of the eye 100, is represented as a module 608 in the reflectometer model 600. Further, spatial coordinates of a simulated environment comprising the module 608 and the physiological model 606, are represented along axes of the reflectometer model 600. For example, a horizontal axis of the reflectometer model 600 represents spatial distance (in metres) along a first dimension (depicted herein as 'y'), and a vertical axis of the reflectometer model 600 represents spatial distance (in metres) along a second dimension (depicted herein as 'z'). Furthermore, the physiological model 606 of the eye 100 includes a first set of parameters, wherein the first set of parameters are values associated with physiological parameters of the eye 100. For example, the first set of parameters of the physiological model 606 of the eye include values of thickness of the cornea 102 of the eye 100, corneal tissue water content, and thickness of the tear film 104 of the eye 100.

Figure 7:
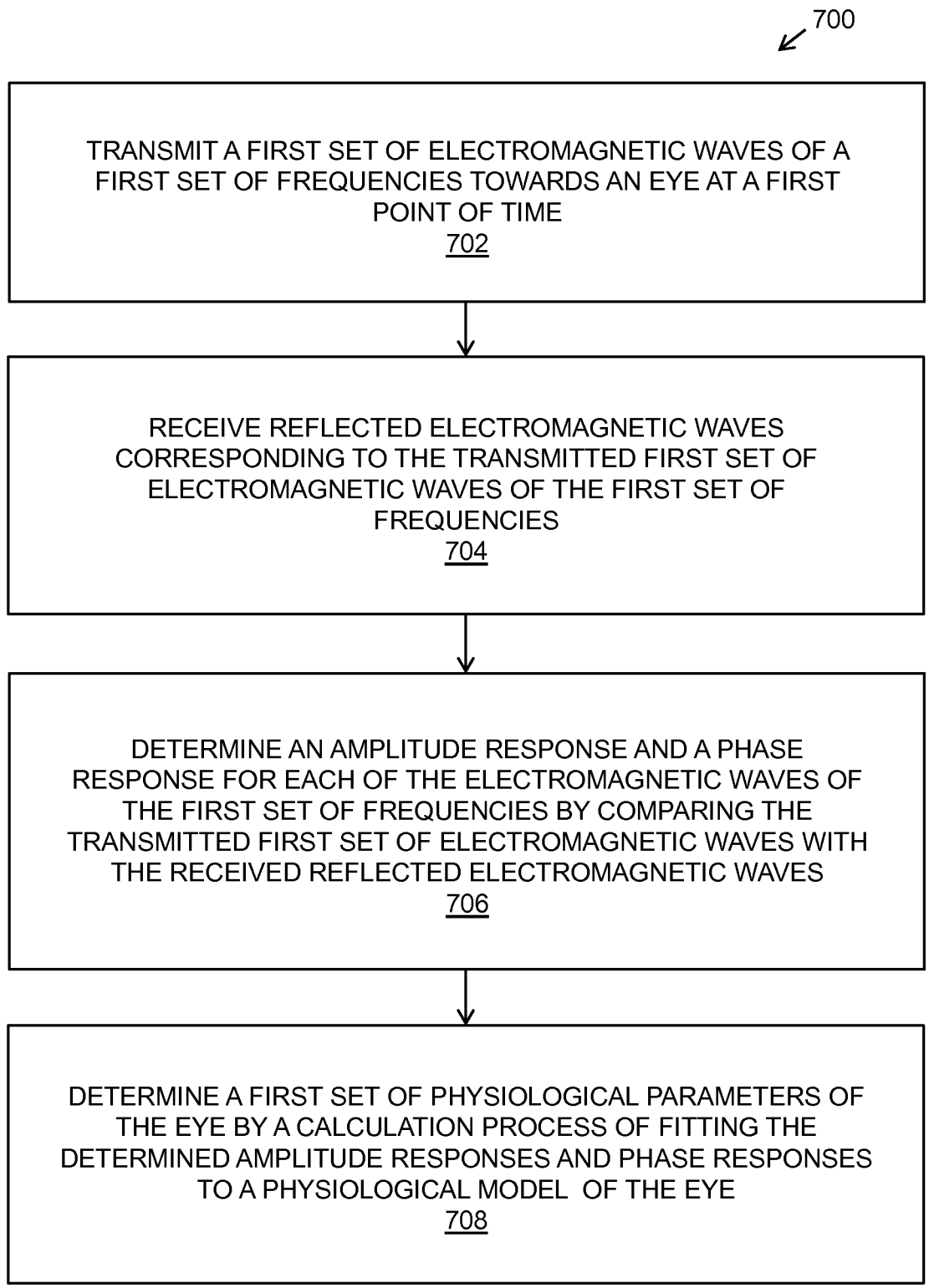
FIG. 7 is an illustration of steps of a method for measuring physiological parameters of an eye, in accordance with an embodiment of the present disclosure.
Figure 8A:
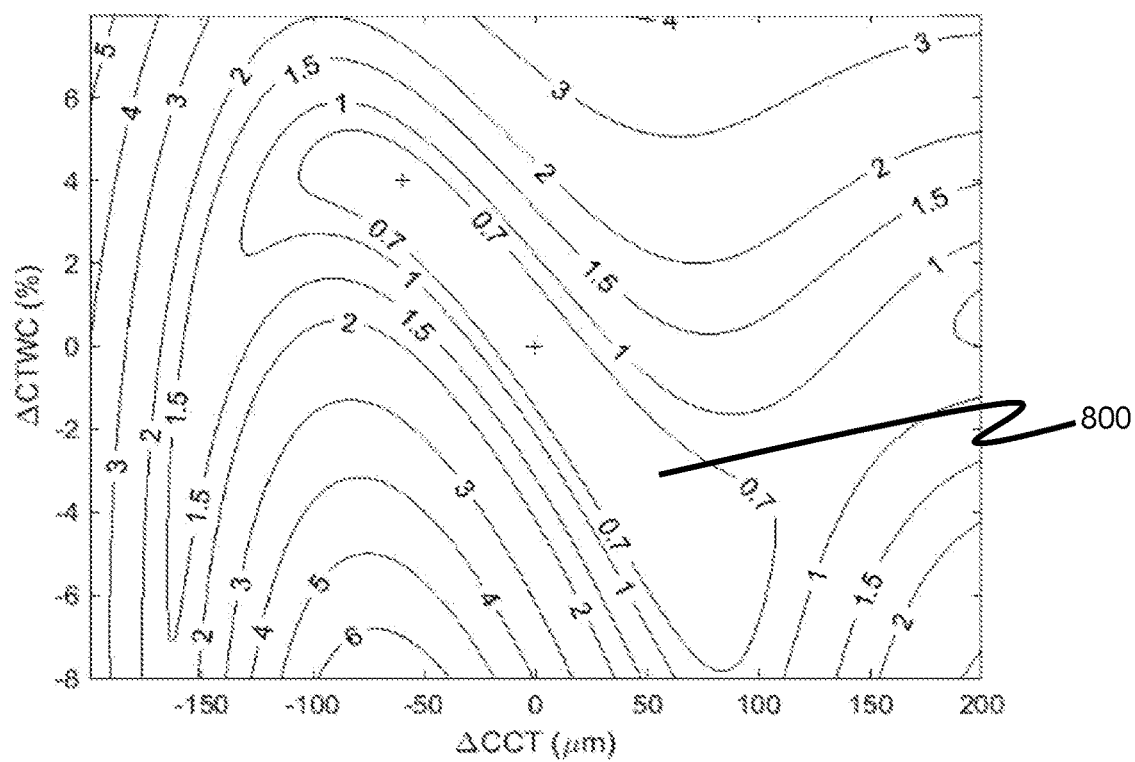
FIGS. 8A and 8B are a first illustration of difference in amplitude and phase when the cornea parameters in a physiological model are changed (the measurement bandwidth is 25 GHz i.e. 200-225 GHz)
Figure 8B:
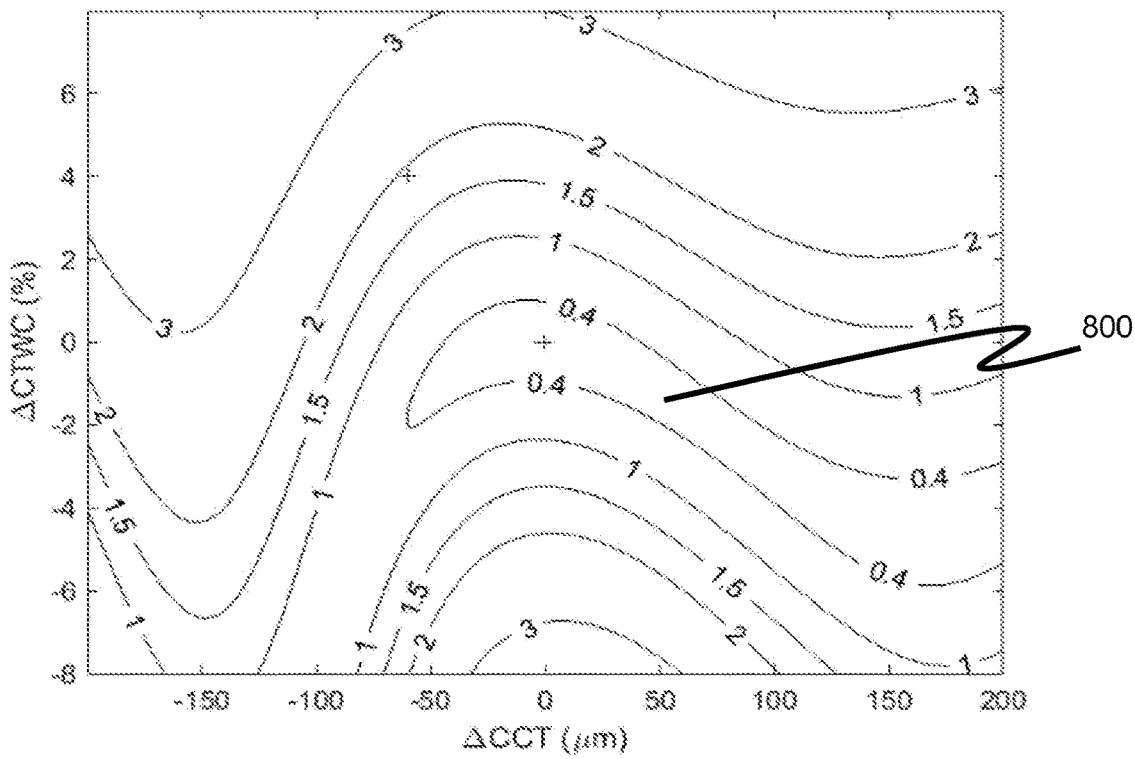
Figure 9A:
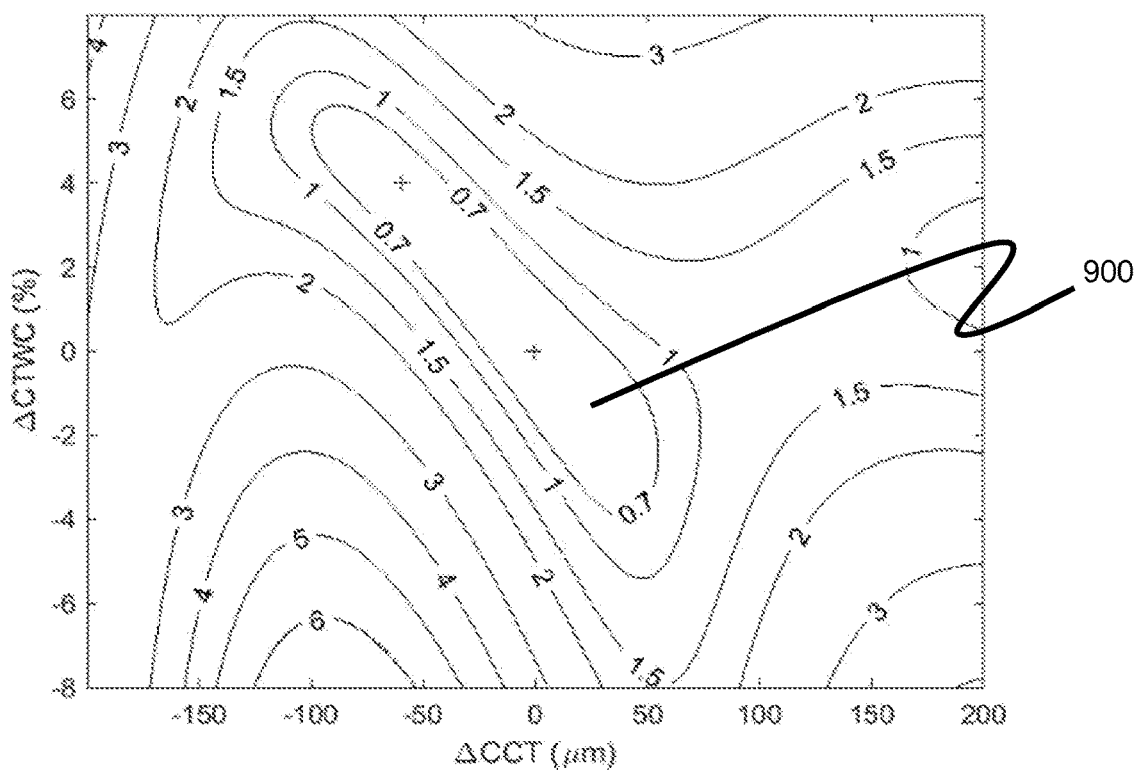
FIGS. 9A and 9B are a second illustration of difference in amplitude and phase when the cornea parameters in a physiological model are changed (the measurement bandwidth is 50 GHz i.e. 200-250 GHz)
Figure 9B:
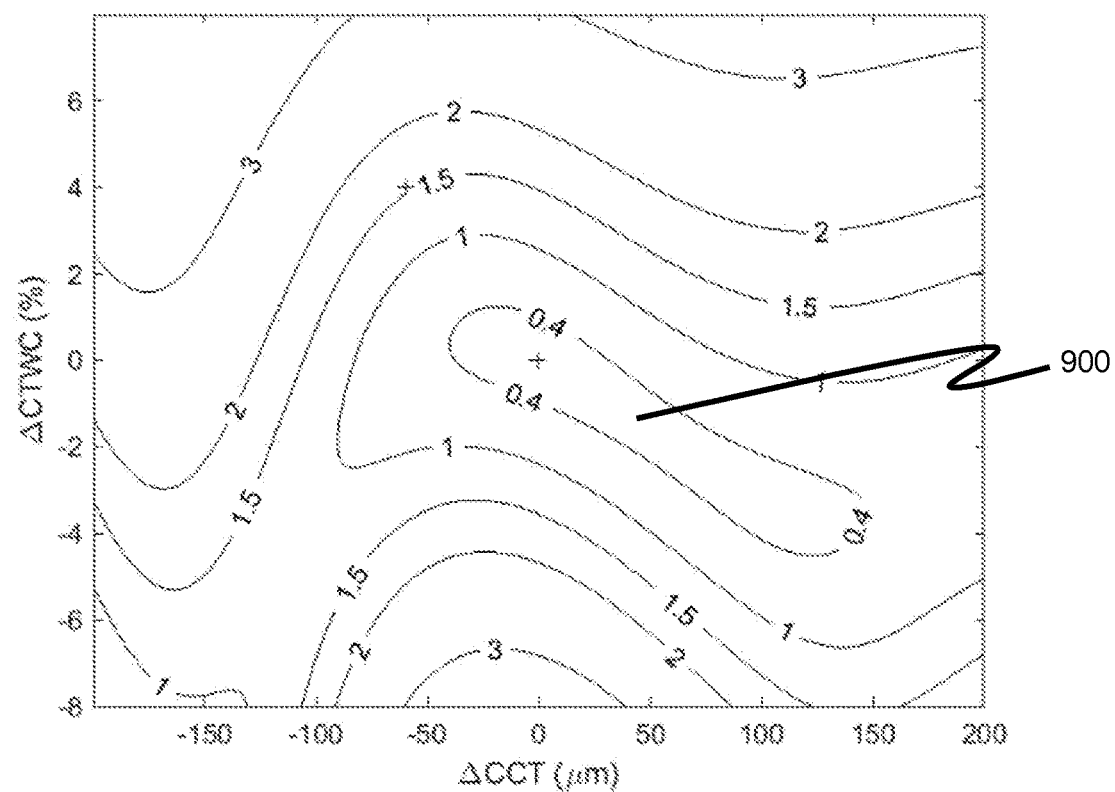
Figure 10A:
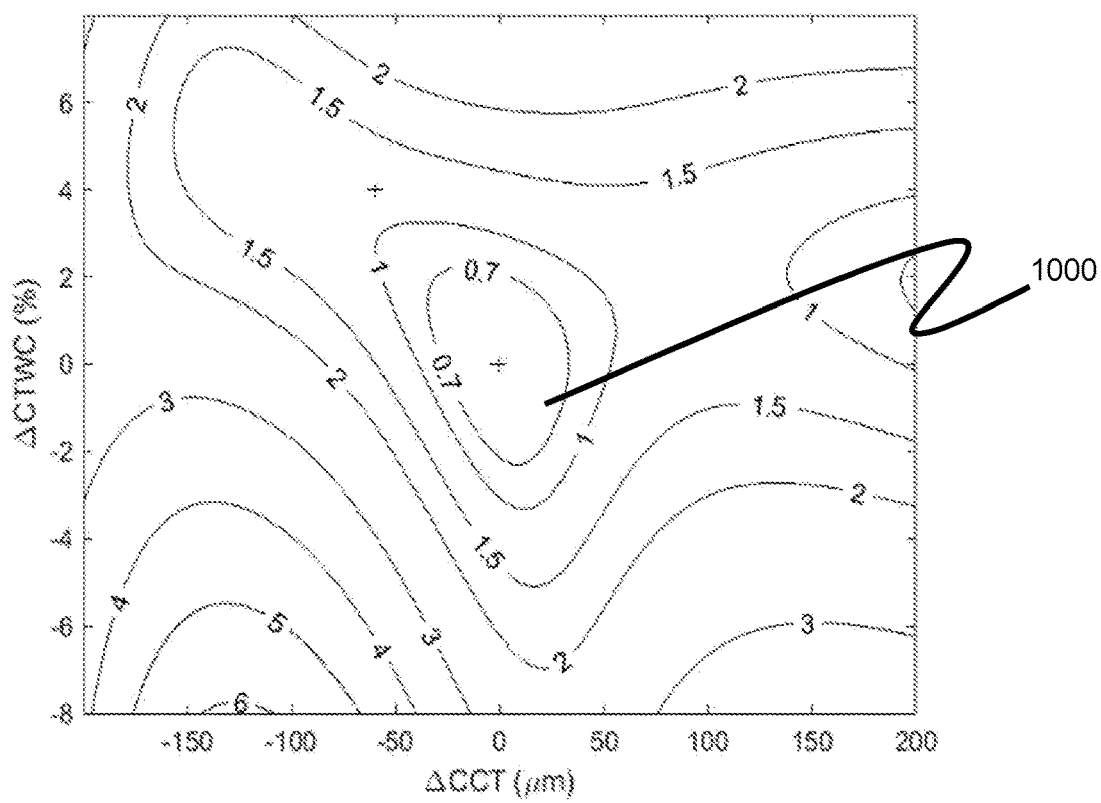
FIGS. 10A and 10B are a third illustration of difference in amplitude and phase when the cornea parameters in a physiological model are changed (the measurement bandwidth is 100 GHz i.e. 200-300 GHz)
Figure 10B:
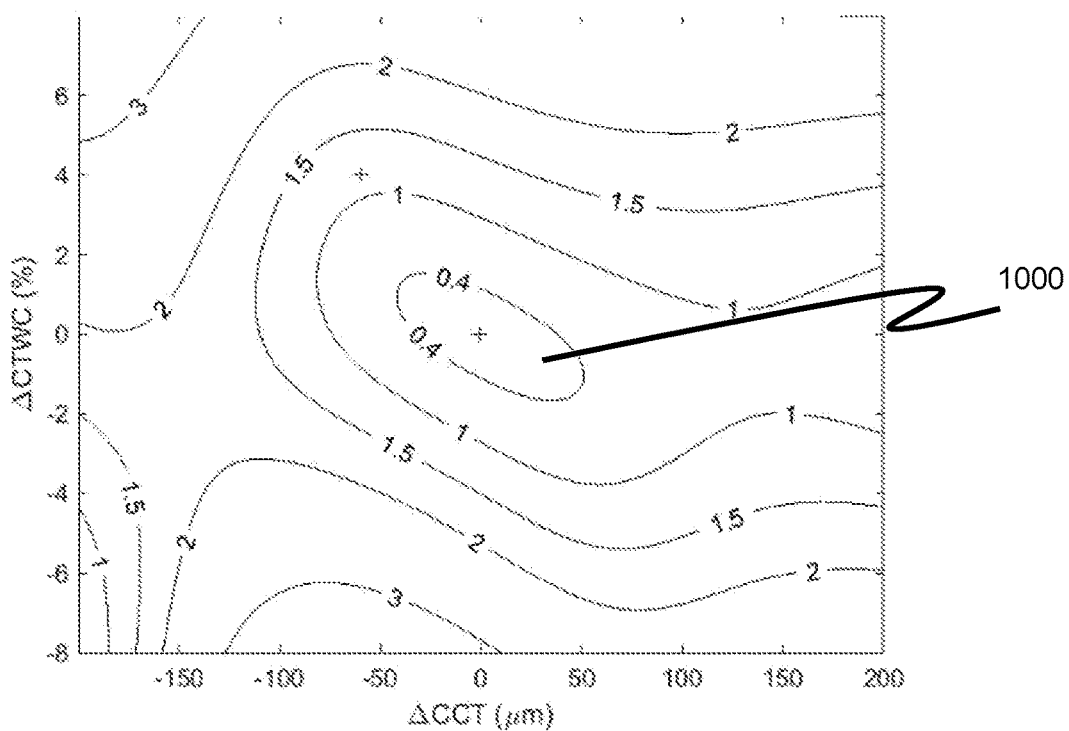
Figure 11A:
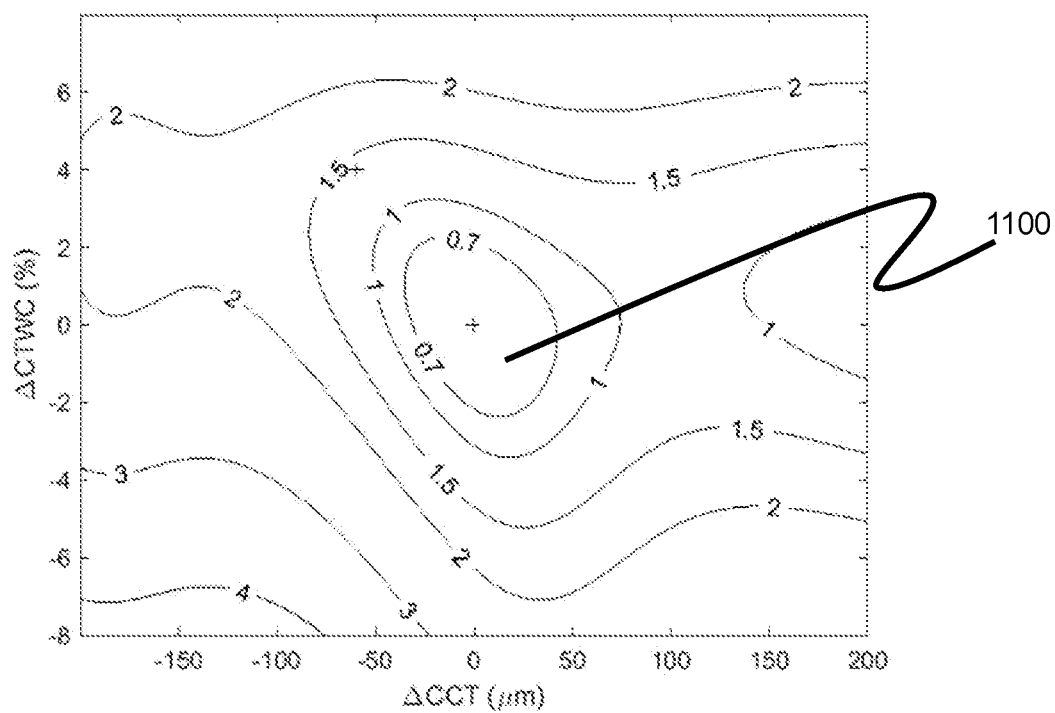
FIGS. 11A and 11B are a fourth illustration of difference in amplitude and phase when the cornea parameters in a physiological model are changed (the measurement bandwidth is 200 GHz i.e. 200-400 GHz)
Figure 11B:
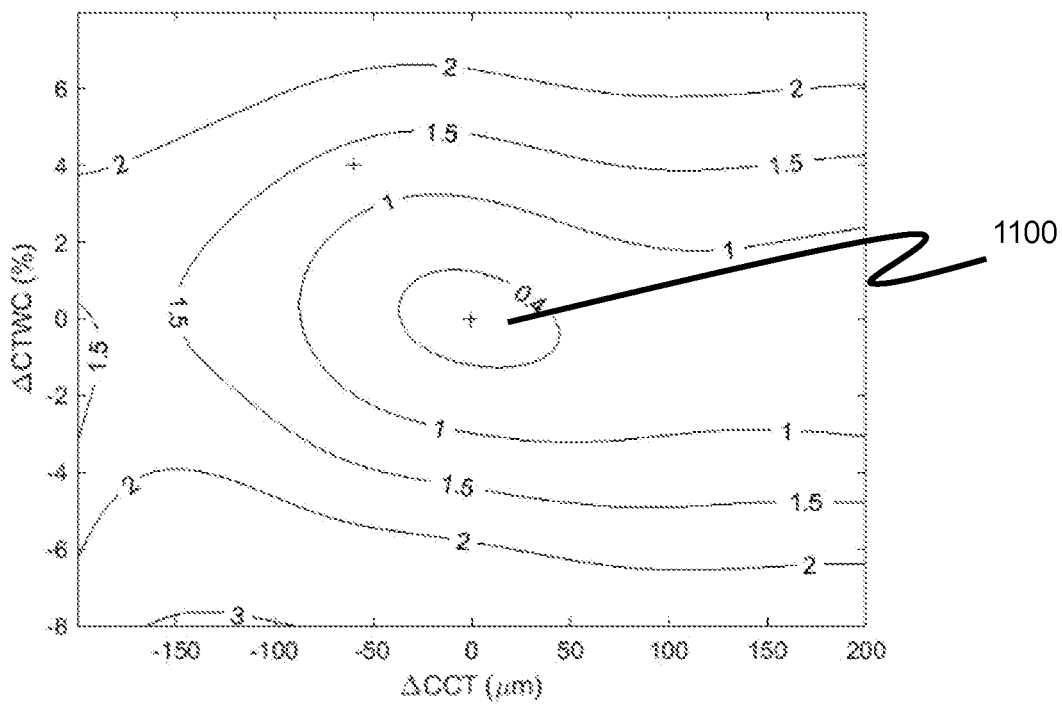

Referring to FIG. 7, illustrated are steps of a method for measuring physiological parameters of an eye (such as the eye 100 of FIG. 1), in accordance with an embodiment of the present disclosure. At step 702, a first set of electromagnetic waves of a first set of frequencies is transmitted towards an eye at a first point of time. At step 704, reflected electromagnetic waves corresponding to the transmitted first set of electromagnetic waves of the first set of frequencies are received. At step 706, an amplitude response and a phase response is determined for each of the electromagnetic waves of the first set of frequencies by comparing the transmitted first set of electromagnetic waves with the received reflected electromagnetic waves. At step 708, a first set of physiological parameters of the eye are determined by a calculation process of fitting the determined amplitude responses and phase responses to a physiological model.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present.

Reference to the singular is also to be construed to relate to the plural.

The invention claimed is:

1. An apparatus for measuring physiological parameters of an eye, comprising
a transmitter for transmitting a first set of electromagnetic waves of a first set of frequencies towards the eye, wherein the transmitter is operable to transmit electromagnetic waves within a frequency range from 100 GHz to 1000 GHz;
a receiver for receiving reflected electromagnetic waves corresponding to the transmitted first set of electromagnetic waves of the first set of frequencies;

wherein it further comprises
- a comparator configured to compare the transmitted first set of electromagnetic waves with the received reflected electromagnetic waves for determining an amplitude response and a phase response for each of the electromagnetic waves of the first set of frequencies; and
- a calculation unit configured to fit the determined amplitude response and phase response to a physiological model of the eye to determine the physiological parameters of the eye.

2. An apparatus according to claim 1, wherein the comparator is configured to determine
- the amplitude response for each of the first set of electromagnetic waves of the first set of frequencies by comparing amplitudes of the transmitted first set of electromagnetic waves with amplitudes of the received reflected electromagnetic waves;
- the phase response for each of the first set of electromagnetic waves of the first set of frequencies by comparing phases of the transmitted first set of electromagnetic waves with phases of the received reflected electromagnetic waves.

3. An apparatus according to claim 2, wherein the transmitter is operable to transmit electromagnetic waves within a frequency range from 200 GHz to 400 GHz.

4. An apparatus according to claim 1, wherein the first set of frequencies is a sweep and the sweep is one of a continuous sweep, a discrete sweep, a broadband sweep or a frequency hopping.

5. An apparatus according to claim 4, wherein the sweep comprises at least one frequency per two unknown parameters in the physiological model of the eye.

6. An apparatus according to claim 1, wherein the physiological parameters are at least one of thickness of a cornea, corneal tissue water content and thickness of tear film.

7. An apparatus according claim 6, of the wherein the physiological parameters further comprise at least one of thickness of cornea epithelium, thickness of Bowman's membrane, thickness of stroma of the cornea, thickness of Dua's layer, thickness of Descemet's membrane and thickness of corneal endothelium.

8. An apparatus according claim 6, of the wherein the physiological parameters further comprise at least one of thickness of lipid layer of the tear film, thickness of water layer of the tear film and thickness of mucus layer of the tear film.

9. An apparatus according to claim 1, wherein the physiological model of the eye is further configured to have a layer in front of the eye, wherein the layer corresponds to contact lens properties.

* * * * *